United States Patent
Jaenisch et al.

(10) Patent No.: US 10,017,744 B2
(45) Date of Patent: *Jul. 10, 2018

(54) METHODS FOR REPROGRAMMING SOMATIC CELLS

(71) Applicant: Whitehead Institute for Biomedical Research, Cambridge, MA (US)

(72) Inventors: Rudolf Jaenisch, Brookline, MA (US); Konrad Hochedlinger, Cambridge, MA (US)

(73) Assignee: WHITEHEAD INSTITUTE FOR BIOMEDICAL RESEARCH, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/588,062

(22) Filed: May 5, 2017

(65) Prior Publication Data

US 2017/0240865 A1 Aug. 24, 2017

Related U.S. Application Data

(60) Continuation of application No. 14/923,321, filed on Oct. 26, 2015, now Pat. No. 9,670,464, which is a continuation of application No. 13/646,430, filed on Oct. 5, 2012, now Pat. No. 9,169,490, which is a continuation of application No. 12/703,061, filed on Feb. 9, 2010, now Pat. No. 8,940,536, which is a division of application No. 10/997,146, filed on Nov. 24, 2004, now Pat. No. 7,682,828.

(60) Provisional application No. 60/525,612, filed on Nov. 26, 2003, provisional application No. 60/530,042, filed on Dec. 15, 2003.

(51) Int. Cl.
C12N 5/00 (2006.01)
C12N 5/074 (2010.01)

(52) U.S. Cl.
CPC ...... *C12N 5/0696* (2013.01); *C12N 2501/602* (2013.01); *C12N 2501/603* (2013.01); *C12N 2501/605* (2013.01); *C12N 2506/1307* (2013.01); *C12N 2510/00* (2013.01)

(58) Field of Classification Search
CPC .......................... C12N 5/0696; C12N 2510/00
See application file for complete search history.

(56) References Cited

U.S. PATENT DOCUMENTS

| | | | |
|---|---|---|---|
| 5,824,837 A | 10/1998 | Chen et al. | |
| 5,843,780 A | 12/1998 | Thomson | |
| 6,200,806 B1 | 3/2001 | Thomson | |
| 7,015,037 B1 | 3/2006 | Furcht et al. | |
| 7,524,677 B2 | 4/2009 | Stockman et al. | |
| 7,601,699 B2 | 10/2009 | Eliertsen | |
| 7,682,828 B2 | 3/2010 | Jaenisch et al. | |
| 7,687,266 B2 | 3/2010 | Chambers et al. | |
| 8,071,369 B2 | 12/2011 | Jaenisch et al. | |
| 8,927,279 B2 | 1/2015 | Jaenisch | |
| 8,932,856 B2 | 1/2015 | Jaenisch | |
| 8,940,536 B2 | 1/2015 | Jaenisch | |
| 8,951,797 B2 | 2/2015 | Jaenisch | |
| 9,169,490 B2 | 10/2015 | Jaenisch | |
| 9,382,515 B2 | 7/2016 | Jaenisch | |
| 9,497,943 B2 | 11/2016 | Jaenisch | |
| 9,670,464 B2 | 6/2017 | Jaenisch | |
| 9,714,414 B2 | 7/2017 | Jaenisch | |
| 2002/0168660 A1 | 11/2002 | Chen et al. | |
| 2004/0137460 A1 | 7/2004 | Yamanaka et al. | |
| 2005/0130144 A1 | 6/2005 | Nakatsuji et al. | |
| 2005/0287547 A1 | 12/2005 | Seligman | |
| 2006/0041946 A1 | 2/2006 | Fisher | |
| 2006/0084172 A1 | 4/2006 | Muller et al. | |
| 2007/0032447 A1 | 2/2007 | Eilersten | |
| 2008/0066197 A1 | 3/2008 | Ying et al. | |
| 2008/0280362 A1 | 11/2008 | Jaenisch et al. | |
| 2009/0047263 A1 | 2/2009 | Yamanaka et al. | |
| 2009/0068742 A1 | 3/2009 | Yamanaka | |
| 2009/0227032 A1 | 9/2009 | Yamanaka et al. | |
| 2010/0062533 A1 | 3/2010 | Yamanaka | |
| 2010/0144031 A1 | 6/2010 | Jaenisch et al. | |
| 2010/0221827 A1 | 9/2010 | Jaenisch et al. | |
| 2010/0310525 A1 | 12/2010 | Chevalier et al. | |
| 2011/0076678 A1 | 3/2011 | Jaenisch et al. | |
| 2011/0151447 A1 | 6/2011 | Park | |
| 2012/0028821 A1 | 2/2012 | Jaenisch et al. | |
| 2012/0034192 A1 | 2/2012 | Young et al. | |
| 2012/0282229 A1 | 11/2012 | Kannemeier et al. | |
| 2013/0017596 A1 | 1/2013 | Townes et al. | |
| 2013/0065311 A1 | 3/2013 | Yamanaka et al. | |
| 2016/0115456 A1 | 4/2016 | Jaenisch | |
| 2017/0067081 A1 | 3/2017 | Jaenisch | |

FOREIGN PATENT DOCUMENTS

| | | |
|---|---|---|
| AU | 2006325975 A1 | 6/2007 |
| CN | 101855350 | 10/2010 |
| EP | 1 970 446 | 9/2008 |
| WO | WO 96/22362 | 7/1996 |
| WO | WO 1999/055841 | 11/1999 |

(Continued)

OTHER PUBLICATIONS

Furler, S., et al. "Recombinant AAV vectors containing the foot and mouth disease virus 2A sequence confer efficient bicistronic gene expression in cultured cells and rat substantia nigra neurons." Gene therapy 8.11 (2001): 864-873.

(Continued)

*Primary Examiner* — Marcia S Noble
(74) *Attorney, Agent, or Firm* — Lisa M. Warren, Esq.; Morse, Barnes-Brown & Pendleton, P.C.

(57) ABSTRACT

The invention provides methods for reprogramming somatic cells to generate multipotent or pluripotent cells. Such methods are useful for a variety of purposes, including treating or preventing a medical condition in an individual. The invention further provides methods for identifying an agent that reprograms somatic cells to a less differentiated state.

9 Claims, 2 Drawing Sheets

(56) References Cited

FOREIGN PATENT DOCUMENTS

| | | |
|---|---|---|
| WO | WO 2000/027995 | 5/2000 |
| WO | WO 2002/097090 | 12/2002 |
| WO | WO 2005/001080 | 1/2005 |
| WO | WO 2005/080598 | 9/2005 |
| WO | WO 2005/090557 | 9/2005 |
| WO | WO 2006/116803 | 11/2006 |
| WO | WO 2007/069666 | 6/2007 |
| WO | WO 2008/001391 A2 | 1/2008 |
| WO | WO 2008/118820 | 10/2008 |
| WO | WO 2008/118820 A2 | 10/2008 |
| WO | WO 2008/124133 A1 | 10/2008 |
| WO | WO 2009/115295 A1 | 9/2009 |
| WO | WO 2009/117439 A2 | 9/2009 |
| WO | WO 2009/133971 | 11/2009 |
| WO | WO 2009/152529 A2 | 12/2009 |
| WO | WO 2010/033920 A2 | 3/2010 |

OTHER PUBLICATIONS

Holst, Jeff, et al. "Generation of T-cell receptor retrogenic mice." Nature protocols 1.1 (2006): 406-417.
Hasegawa, Kouichi, et al. "Efficient multicistronic expression of a transgene in human embryonic stem cells." Stem cells 25.7 (2007): 1707-1712.
Szymczak, Andrea L., et al. "Correction of multi-gene deficiency in vivo using a single 'self-cleaving' 2A peptide—based retroviral vector." Nature biotechnology 22.5 (2004): 589-594.
Corrected Notice of Allowability in U.S. Appl. No. 14/473,250, dated Jun. 6, 2017.
Notice of Allowance and Fee(s) Due in U.S. Appl. No. 14/473,250, dated May 30, 2017.
Aoi, et al., "Generation of Pluripotent Stem Cells from Adult Mouse Liver and Stomach Cells", Science, 321: 699-702 (2008).
Avilion, et al., "Multipotent cell lineages in early mouse development depend on SOX2 function", Genes & Development, 17:126-140 (2003).
Ben-Shushan, et al., "Extinction of Oct-3/4 gene expression in embryonal carcinoma x fibroblast somatic cell hybrids is accompanied by changes in the methylation status, chromatin structure, and transcriptional activity of the Oct-3/4 upstream region", Molecular and Cellular Biology, 13(2):891-901 (1993).
Bortvin, et al., "Incomplete Reactivation of Oct4-related in Mouse Embryos Cloned from Somatic Nuclei", Development, 130:1673-1680 (2003).
Boyer, et al., "Polycomb complexes repress developmental regulators in murine embryonic stem cells", Nature, 441(7091):349-353 (2006).
Brambrink, et al., "Sequential Expression of Pluripotency Markers During Direct Reprogramming of Mouse Somatic Cells", Cell Stem Cell, 2(2): 151-159 (2008).
Bronson, et al., "Single-copy transgenic mice with chosen-site integration", Proc. Natl. Acad. Sci. USA, 93:9067-9072 (1996).
Bru, et al., "Rapid induction of pluripotency genes after exposure of human somatic cells to mouse ES cell extracts", Experimental Cell Research, 314:2634-2642 (2008).
Buske, et al., "Overexpression of HOXA10 perturbs human lymphomyelopoiesis in vitro and in vivo", Blood, 97(8):2286-2292 (2001).
Carey, et al., "Reprogramming of murine and human somatic cells using a single polycistronic vector", Proceedings of the National Academy of Science, 106:157-162 (2008).
Chambers, et al., "Functional expression cloning of nanog, a pluripotency sustaining factor in embryonic stem cells", Cell, 113:643-655 (2003).
Chen, et al., "Establishment and Maintenance of Genomic Methylation Patterns in Mouse Embryonic Stem Cells by Dnmt3a and Dnmt3b", Molecular and Cellular Biology, 23(16):5594-5605 (2003).

Daniels, et al., "Analysis of Gene Transcription in Bovine Nuclear Transfer Embryos Reconstructed with Granulosa Cell Nuclei", Biology of Reproduction, 63:1034-1040 (2000).
Eminli, et al., "Reprogramming of Neural Progenitor Cells into iPS Cells in the Absence of Exogenous Sox2 Expression", Stem Cells, 26:2467-2474 (2008).
Gossen, et al., "Transcriptional activation by tetracyclines in mammalian cells", Science, 268(5218):1766-1769 (1995).
Greiner, et al., "Identification of a specific inhibitor of the histone methyltransferase SU(VAR)3-9", Nature Chemical Biology, 1:143-145 (2005).
Hanna, et al. "Direct reprogramming of terminally differentiated mature B lymphocytes to pluripotency", Cell 133, 250-264 (2008).
Hansis, et al., "Analysis of Oct-4 expression and ploidy in individual human blastomeres", Molecular Human Reproduction, 7: 155-161 (2001).
Hasegawa, et al., "Efficient multicistronic expression of a transgene in human embryonic stem cells," Stem Cells, 25(7): 1707-1712 (2007).
Helgason, et al., "Overexpression of HOXB4 enhances the hematopoietic potential of embryonic stem cells differentiated in vitro", Blood, 87(7):2740-2749 (1996).
Ho, et al., "Synthetic Protein Transduction Domains: Enhanced Transduction Potential in Vitro and in Vivo," Cancer Research, 61: 474-477 (2001).
Hochedlinger, et al., "Monoclonal mice generated by nuclear transfer from mature B and T donor cells", Nature, 415:1035-1038 (2002).
Hochedlinger, et al., "Nuclear transplantation, embryonic stem cells, and the potential for cell therapy", The New England Journal of Medicine, 349(3):275-286 (2003).
Ihle, et al., "STATs: Signal Transducers and Activators of Transcription", Cell, 84: 331-334 (1996).
Jackson-Grusby, et al., "Loss of Genomic Methylation Cases p53-Dependent Apoptosis and Epigenetic Deregulation", Nature Genetics, 27: 31-39 (2001).
Jaenisch, et al., "Nuclear cloning, stem cells, and genomic reprogramming", Cloning and Stem Cells, 4(4):389-396 (2002).
Jaenisch & Young, "Stem Cells, the Molecular Circuitry of Pluripotency and Nuclear Reprogramming", Cell, 132, 567-582 (2008).
Kaufman, et al., "Hematopoietic colony-forming cells derived from human embryonic stem cells", PNAS, 98(19):10716-10721 (2001).
Kubicek, et al., "Reversal of H3K9me2 by a small-molecule inhibitor for the G9a histone methyltransferase", Molecular Cel, 25(3):473-81 (2007).
Kyba et al., "HoxB4 confers definitive lymphoid-myeloid engraftment potential on embryonic stem cell and yolk sac hematopoietic progenitors", Cell, 109:29-37 (2002).
Lenardo et al., "Repression of the IgH Enhancer in Teratocarcinoma Cells Associated with a Novel Octamer Factor", Science, New Series, 243(4890):544-546 (1989).
Li, et al., "Murine embryonic stem cell differentiation is prompted by SOCS-3 and inhibited by the zinc finger transcription factor Klf4", Blood, 105:635-637 (2005).
Loh, et al., "The Oct4 and Nanog transcription network regulates pluripotency in mouse embryonic stem cells", Nature Genetics, 38(4): 431-440 (2006).
Lowry, et al. Generation of human induced pluripotent stem cells from dermal fibroblasts. "PNAS", 105(8):2883-2888 (2008).
Ma, et al., "G9a and Jhdma2a Regulate Embryonic Stem Cell Fusion-Induced Reprogramming of Adult Neural Stem Cells", Stem Cells, 26)8): 2131-2141 (2008).
Matsuoka, et al., "Generation of definitive hematopoietic stem cells from murine early yolk sac and paraaortic splanchnopleures by aorta-gonad-mesonephros region-derived stromal cells", Blood, 98(1):6-12 (2001).
McWhir, et al., "Selective ablation of differentiated cells permits isolation of embryonic stem cell lines from murine embryos with a non-permissive genetic background", Nature Genetics, 14:223-226 (1996).

(56) References Cited

OTHER PUBLICATIONS

Mitsui et al., "The Homeoprotein Nanog is Required for Maintenance of Pluripotency in Mouse Epiblast and ES Cells", *Cell*, 113: 631-642 (2003).
Mountford, et al., "Dicistronic targeting constructs: Reporters and modifiers of mammalian gene expression", *Proceedings of the National Academy of Sciences*, 91: 4303-4307 (1994).
Munsie, et al., "Transgenic strategy for demonstrating nuclear reprogramming in the mouse", *Cloning Stem Cells*, 4(2):121-130 (2002).
Naito, et al., Journal of Reproduction and Fertility 113:137-143 (1998).
Nichols, et al., "Formation of Pluripotent Stem Cells in the Mammalian Embryo Depends on the POU Transcription Factor Oct4", *Cell*, 95: 379-391 (1998).
Niwa, et al., "Quantitative expression of Oct-3/4 defines differentiation, dedifferentiation or self-renewal of ES cells", *Nature Genetics*, 24: 372-376 (2000).
Okita, et al., "Generation of Mouse Induced Pluripotent Stem Cells Without Viral Vectors", *Science*, 322:949-953 (2008).
Peled, et al., "Dependence of human stem cell engraftment and repopulation of NOD/SCID mice on CXCR4", *Science*, 283:845-848 (1999).
Pesce, et al., "Oct-4: Gatekeeper in the beginnings of mammalian development", *Stem Cells*, 19:271-278 (2001).
Qi, et al., "The magic of four: induction of pluripotent stem cells from somatic cells by Oct4, Sox2, Myc and Klf4", *Cell Research*, 17:578-580 (2007).
Radcliffe, et al., "Multiple gene products from a single vector: 'self-cleaving' 2A peptides", *Gene Therapy*, 11:1673-1674 (2004).
Ramalho-Santos, et al., "Stemness: Transcriptional Profiling of Embryonic and Adult Stem Cells", *Science*, 298: 597-600 (2002).
Ryan, et al., "Cleavage of foot-and-mouth disease virus polyprotein is mediated by residues located within a 19 amino acid sequence", *Journal of General Virology*, 72:2727-2732 (1991).
Savarese, et al., "Hematopoletic Precursor Cells Transiently Reestablish Permissiveness for X Inactivation", *Molecular and Cellular Biology*, 26(19): 7167-7177 (2006).
Sells, et al., "Delivery of Protein into Cells Using Polycationic Liposomes," *BioTechniques* 19(1):72-78 (1995).
Shields, et al., "Identification and Characterization of a Gene Encoding a Gut-Enriched Kruppel-like Factor Expressed during Growth Arrest", *Journal of Biological Chemistry*, 271(33):20009-20017 (1996).
Stacey, et al., "Microinjection of Transforming ras Protein Induces c-fos Expression," *Molecular and Cellular Biology*, 7(1): 523-527 (1987).
Stadfeld, et al., "Reprogramming of Pancreatic β Cells into Induced Pluripotent Stem Cells", *Current Biology*, 18:890-894 (2008).
Stem Cells: Scientific Progress and Future Research Directions. Department of Health and Human Services. Jun. 2001, </info/scireport/2001report>. Chapter 4: The Adult Stem Cell, pp. 23-42.
Tada, et al., "Nuclear Reprogramming of Somatic Cells by In Vitro Hybridization with ES cells", *Current Biology*, 11: 1553-1558 (2001).
Takahashi, et al., "Induction of Pluripotent Stem Cells from Adult Human Fibroblasts by Defined Factors", *Cell*, 131, 861-872 (2007).
Takahashi, et al., "Induction of Pluripotent Stem Cells from Mouse Embryonic and Adult Fibroblast Cultures by Defined Factors", *Cell*, 126: 663-676 (2006).
Thomson, et al., "Embryonic Stem Cell Lines Derived from Human Blastocysts", *Science*, 282, 1145-1147 (1998).
Wadia, et al., "Protein Transduction Technology," *Analytical Biotechnology*, 13: 52-56 (2002).
Wernig, et al., "A drug-inducible transgenic system for direct reprogramming of multiple somatic cell types", *997 Biotechnology*, 26(8):916-924 (2008).
Wernig, et al., "In vitro reprogramming of fibroblasts into a pluripotent ES-cell-like state", *Nature*, 448: 318-324 (2007).
Wernig, et al., "Neurons derived from reprogrammed fibroblasts functionally integrate into the fetal brain and improve symptoms of rats with Parkinson's disease", *PNAS*, 105(15):5856-5861 (2008).
Yamanaka, et al., "Strategies and New Developments in the Generation of Patient-Specific Pluripotent Stem Cells", *Cell Stem Cell*, 1: 39-49 (2007).
Yeom et al., "Germline regulatory element of Oct-4 specific for the totipotent cycle of embryonal cells," *Development*,122:881-897 (1996).
Ying, et al., "BMP induction of Id proteins suppresses differentiation and sustains embryonic stem cell self-renewal in collaboration with STAT3", *Cell*, 115: 281-292 (2003).
Yoshimizu, et al., "Germline-specific expression of the Oct-4/green fluorescent protein (GFP) transgene in mice", *Development, Growth & Differentiation*, 41:675-684 (1999).
Yu, et al., "Induced pluripotent stem cell lines derived from human somatic cells", *Science*, 318(5858):1917-20 (2007).
Zakhartchenko, et al., "Adult cloning in cattle: potential of nuclei from a permanent cell line and from primary cultures", *Molecular Reproduction and Development*, 54:264-272 (1999).
Zambrowicz, et al., "Disruption of overlapping transcripts in the ROSA βgeo 26 gene trap strain leads to widespread expression of β-galactosidase in mouse embryos and hematopoietic cells", *Proc. Natl. Acad. Sci. USA*, 94:3789-3794 (1987).
Zhou, et al., "Generation of Induced Pluripotent Stem Cells Using Recombinatnt Proteins", *Cell Stem Cell*, 4:381-384 (2009).
Blast Alignment Seq Id 16 (ECAT4).
Sox2. Print out from Pubmed http://www.ncbi.nlm.nih.gov/nuccore/127140985?ordinalp...ntrez.Sequence.
Sequence_ResultsPanel.Sequence_RVDocSum p. 1-6, printed Apr. 7, 2009.
Nanog. Printout from Pubmed http://www.ncbi.nlm.nih.gov/nuccore/153791181?ordinalp...netrez.Sequence.
Sequence_ResultsPanel.Sequence_RVDocSum p. 1-6, printed Apr. 7, 2009.
Scholer, et al., "New type of POU domain in germ line-specific protein Oct-4", Letters to Nature, 344: 435-439 (1990).
Bilic, et al., "Concise Review: Induced Pluripotent Stem Cells Versus Embryonic Stem Cells: Close Enough or Yet Too Far Apart?", *Stem Cells*, 30:33-41(2012).
Chin, et al., "Induced Pluripotent Stem Cells and Embryonic Stem Cells are Distinguished by Gene Expression Signatures", *Cell Stem Cell*, 5:111-123(2009).
Chin, et al., "Molecular Analyses of Human Induced Pluripotent Stem Cells and Embryonic Stem Cells", *Cell Stem Cell*, 7(2):263-269(2010).
Munoz, et al., "The Quantitative Proteomes of Human-Induced Pluripotent Stem Cells and Embryonic Stem Cells", *Molecular Systems Biology*, 7(550): 1-13(2011).
Polouliakh, et al., "Reprogramming Resistant Genes: In-Depth Comparison of Gene-Expressions Among iPS, ES, and somatic cells", *Frontiers in Physiology*, 4(7):1-9(2013).
Meissner, et al., "Direct Reprogramming of genetically unmodified fibroblasts into pluripotent stem cells", *Nature Biotechnology*, 25(10): 1177-1181 (2007).
Strelchenko, et al. "Reprogramming of human somatic cells by embryonic stem cell cytoplast", *Reprod. Biomed Online*, 12(1): 107-111 (2006).
Cowan, et al., Nuclear Reprogramming of Somatic Cells After Fusion with Human Embryonic Stem Cells, *Science*, 309:1369-1373 (2005).
Laiosa, et al., "Reprogramming of Committed T Cell Progenitors to Macrophages and Dendritic Cells by C/EBPa and PU.1 Transcription Factors", *Immunity*, 25: 731-744 (2006).
Ait-Si-Ali, et al., "A Suv39h-dependent mechanism for silencing S-phase genes in differentiating but not in cycling cells", *EMBO Journal*, 23:605-615 (2004).
Maherali, et al., "Directly Reprogrammed Fibroblasts Show Global Epigenetic Remodeling and Widespread Tissue Contribution", Cell Stem Cell, 1:55-70(2007).
Sarraf, et al., "Methyl-CpG Binding Protein MBD1 Couples Histone H3 Methylation at Lysine 9 by SETDB1 to DNA Replication and Chromatin Assembly", Molecular Cell, 15:595-605 (2004).

(56) References Cited

OTHER PUBLICATIONS

PubMed Oct4 gene, Printout from www.ncbi.nlm.nih.gov/nuccore/NM_013633.3, pp. 1-12, Sep. 19, 2013.
Palmqvist, et al., "Correlation of Murine Embryonic Stem Cell Gene Expression Profiles with Functional Measures of Pluripotency", Stem Cells, 23:663-680 (2005).
Yu, et al., "Induced pluripotent stem cell lines derived from human somatic cells", Science, 318:1917-1920 (2007).
Sox2 cDNA, printout from http://ncbi.nih.gov/nuccor/BC057574.1, pp. 1-13 (2013).
Oct4 cDNA, printout from http://ncbi.nih.gov/nuccor/BC117437.1, pp. 1-10 (2013).
Chinnasamy, et al., "Multicistronic lentiviral vectors containing the FMDV 2A cleavage factor demonstrate robust expression of encoded genes at limiting MOI", *Virology Journal*, 3: 14-29 (2006).
Okita, et al., "Generation of germline-competent induced pluripotent stem cells", *Nature*, 448: 313-318 (2007).
Feldman, et al., "G9a-mediated irreversible epigenetic inactivation of Oct-3/4 during early embryogenesis", *Nature Cell Biology*, 455: 627-633 (2008).
Zhou, et al., "In vivo reprogramming of adult pancreatic exocrine cells to b-cells", *Nature*, 455: 627-633 (2008).
Kong, et al., "Lack of specificity of fibroblast-specific protein 1 in cardiac remodeling and fibrosis", *American Journal of Physiology Heart and Circulatory Physiology*, 305: H1363-1372 (2013).
Nakagawa, et al., "Generation of induced pluripotent stem cells without Myc from mouse and human fibroblasts", *Nature Biotechnology*, 26(1): 101-106 (2008).
Silva, et al., "Nanog promotes transfer of pluripotency after cell fusion", *Nature*, 441: 997-1001 (2006).
Shi, et al., Dynamic Regulation of Histone Lysine Methylation by Demethylases, *Molecular Cell*, 26995: 1-14 (2007).
Fawell, et al., "Tat-Mediated delivery of heterologous proteins into cells", *Proceedings of the National Academy of Science*, 91: 664-668 (1994).
Cavaleri, et al., "Nanog: a New Recruit to the Embryonic Stem Cell Orchestra", Cell 113: 551-557 (2003).
Stevanovic, et al., "The cDNA sequence and chromosomal location of the human SOX2 gene", Mammalian Genome 5: 640-642 (1994).
Grinnell, et al., "De-Differentiation of Mouse Interfollicular Keratinocytes by the Embryonic Transcription Factor Oct-4", *Journal of Investigative Dermatology*, 127; 372-380 (2007).
Kim, et al., "Oct4-Induced Pluripotency in Adult Neural Stem Cells," Cell, 136:411-419 (2009).
Patel et al., "Advances in Reporgramming Somatic Cells to Induced Pluripotent Stem Cells," NIH Public Access Author Manuscript, Jan. 1, 2011 (online) [retrieved from internet May 3, 2015] URL:http://ncbi.nih.gov/pmc/articles/PMC2924949/pdf/nihms-219126.pdf published in final edited form as: Stem Cell Reviews 6(3): 367-380 (Sep. 2010).
Jaenisch, Rudolf, Abstract "In vitro reprogramming of somatic cells into pluripotent ES-like cells", National Institutes of Health Grant No. 4R37 HD045022-11 through 4R37 HD045022-14, Funding Dates 2013 through 2016.
Jaenisch, Rudolf, Abstract "In vitro reprogramming of somatic cells into pluripotent ES-like cells", National Institutes of Health Grant No. 2R01 HD045022-06 through 4R37 HD045022-10, Funding Dates 2008 through 2012.
Jaenisch, Rudolf, Abstract "Nuclear Cloning and the Reprogramming of the Genome" National Institutes of Health Grant No. 1R01 HD045022-01 through 5R01 HD045022-05, Funding Dates 2003 through 2007.
Jaenisch, Rudolf, Abstract "Programming and Reprogramming Human Cells" National Institutes of Health Grant No. 2R01 CA084198-10 through 5R01 CA084198-14, Funding Dates 2009 through 2013.
Jaenisch, Rudolf, Abstract "Genomic Imprinting and the Cloning of Mice" National Institutes of Health Grant No. 1R37 CA084198-01 through 5R37 CA084198-09, Funding Dates 2000 through 2008.

Jaenisch, Rudolf, Abstract Epigenetics, stem cells, and cancer National Institutes of Health Grant Nos. 2RO1 CA087869-06 through 5RO1 CA087869-10, Funding Dates 2006 through 2010.
Jaenisch, Rudolf, Abstract "DNA Methylation, Gene Regulation, and Cancer" National Institutes of Health Grant Nos. 1RO1 CA087869-01 through 5RO1 CA087869-05, Funding Dates 2001 through 2005.
Young, Richard, Abstract "Transcriptional Regulatory Networks in Living Cells" National Institutes of Health Grant No. 2RO1 HG002668-11A1 through 5RO1 HG002668-13, Funding Dates 2014 through 2016.
Young, Richard, Abstract "Transcriptional Regulatory Networks in Living Cells" National Institutes of Health Grant No. 2RO1 HG002668-07 through 3RO1 HG002668-10S1, Funding Dates 2010 through 2013.
Young, Richard, Abstract "Transcriptional Regulatory Networks in Living Cells" National Institutes of Health Grant No. 2RO1 HG002668-04A1 through 5RO1 HG002668-06, Funding Dates 2007 through 2009.
Young, Richard, Abstract "Transcriptional Regulatory Network in Living Cells" National Institutes of Health Grant No. 1 RO1 HG002668-01 through 3RO1 HG002668-03S1, Funding Dates 2003 through 2006.
De Felipe, P., "Polycistronic Viral Vectors," Current Gene Therapy, 2002, vol. 2, No. 3, pp. 355-378.
Wernig, Marius, et al. "c-Myc is dispensable for direct reprogramming of mouse fibroblasts." *Cell stem cell* 2.1 (2008): 10-12.
International Search Report for International Application PCT/US08/04516, dated Sep. 10, 2008.
International Search Report for International Application PCT/US2009/047423, dated May 3, 2010.
International Search Report for International Application PCT/US2009/057692, dated Jun. 30, 2010.
Supplementary European Search Report for Application No. EP 08742630.0, dated Mar. 25, 2010.
Supplementary European Search Report for Application No. EP 09763816, dated Nov. 29, 2012.
Partial European Search Report for Application No. EP12003893, dated Jun. 24, 2013.
Non-Final Office Action for U.S. Appl. No. 10/997,146, dated Nov. 3, 2006.
Final Office Action for U.S. Appl. No. 10/997,146, dated Aug. 14, 2007.
Non-Final Office Action for U.S. Appl. No. 10/997,146, dated Jul. 22, 2008.
Non-Final Office Action for U.S. Appl. No. 10/997,146, dated Apr. 9, 2009.
Non-Final Office Action for U.S. Appl. No. 12/703,015, dated Oct. 28, 2010.
Final Office Action for U.S. Appl. No. 12/703,015, dated Jul. 8, 2011.
Non-Final Office Action for U.S. Appl. No. 12/703,061, dated Oct. 28, 2010.
Final Office Action for U.S. Appl. No. 12/703,061, dated Jul. 14, 2011.
Non-Final Office Action for U.S. Appl. No. 12/703,061, dated Sep. 19, 2011.
Notice of Allowance in U.S. Appl. No. 10/997,146, dated Jan. 26, 2010.
Notice of Allowance in U.S. Appl. No. 12/703,015, dated Sep. 16, 2011.
Non-Final Office Action for U.S. Appl. No. 12/595,041, dated May 9, 2012.
Final Office Action for U.S. Appl. No. 12/595,041, dated Dec. 7, 2012.
Non-Final Office Action for U.S. Appl. No. 13/646,411, dated Feb. 27, 2013.
Non-Final Office Action for U.S. Appl. No. 13/119,891, dated May 15, 2013.
Non-Final Office Action for U.S. Appl. No. 12/703,061, dated Aug. 20, 2013.
Non-Final Office Action for U.S. Appl. No. 13/646,444, dated Aug. 20, 2013.

(56) References Cited

OTHER PUBLICATIONS

Non-Final Office Action for U.S. Appl. No. 13/646,430, dated Sep. 20, 2013.
Non-Final Office Action for U.S. Appl. No. 13/646,420, dated Sep. 23, 2013.
Non-Final Office Action for U.S. Appl. No. 12/595,041, dated Oct. 2, 2013.
Non-Final Office Action for U.S. Appl. No. 13/646,411, dated Oct. 31, 2013.
Non-Final Office Action for U.S. Appl. No. 13/119,891, dated Jan. 2, 2014.
Non-Final Office Action for U.S. Appl. No. 12/997,815, dated Jan. 3, 2014.
Final Office Action for U.S. Appl. No. 13/646,430, dated Apr. 1, 2014.
Final Office Action for U.S. Appl. No. 13/646,444, dated Apr. 2, 2014.
Final Office Action for U.S. Appl. No. 13/646,420, dated Apr. 2 2014.
Final Office Action for U.S. Appl. No. 12/703,061, dated Apr. 11, 2014.
Final Office Action for U.S. Appl. No. 13/646,411, dated May 9, 2014.
Non-Final Office Action for U.S. Appl. No. 13/646,420, dated May 27, 2014.
Final Office Action for U.S. Appl. No. 12/595,041, dated May 30, 2014.
Final Office Action for U.S. Appl. No. 12/997,815, dated Jul. 15, 2014.
Final Office Action for U.S. Appl. No. 13/119,891, dated Aug. 18, 2014.
Notice of Allowance for U.S. Appl. No. 12/703,061, dated Nov. 7, 2014.
Notice of Allowance for U.S. Appl. No. 13/646,411, dated Dec. 8, 2014.
Notice of Allowance for U.S. Appl. No. 13/646,420, dated Sep. 17, 2014.
Non-Final Office Action for U.S. Appl. No. 13/646,430, dated Dec. 8, 2014.
Non-Final Office Action for U.S. Appl. No. 12/595,041, dated Apr. 3, 2015.
Non-Final Office Action for U.S. Appl. No. 12/997,815, dated May 19, 2015.
Notice of Allowance for U.S. Appl. No. 13/646,430, dated Jun. 18, 2015.
Non-Final Office Action for U.S. Appl. No. 14/473,250, dated Aug. 25, 2015.
Final Office Action for U.S. Appl. No. 12/595,041, dated Oct. 30, 2015.
Final Office Action for U.S. Appl. No. 12/997,815, dated Feb. 19, 2016.
Notice of Allowance for U.S. Appl. No. 12/595,041, dated Mar. 7, 2016.
Notice of Allowance for U.S. Appl. No. 13/646,444, dated Sep. 22, 2014.
Final Office Action for U.S. Appl. No. 14/473,250, dated Apr. 26, 2016.
Notice of Allowance for U.S. Appl. No. 12/997,815, dated Jun. 30, 2016.
Notice of Allowance for U.S. Appl. No. 14/473,250, dated May 30, 2017.
Non-Final Office Action for U.S. Appl. No. 14/923,321, dated Aug. 2, 2016.
Final Office Action for U.S. Appl. No. 14/923,321 dated Jan. 4, 2017.
Notice of Allowance for U.S. Appl. No. 14/923,321 dated Mar. 24, 2017.
Non-Final Office Action for U.S. Appl. No. 15/607,028, dated Sep. 20, 2017.
Final Office Action in U.S. Appl. No. 15/607,028, dated Feb. 14, 2018.
Griffiths, Anthony J.F., et al., "An Introduction to Genetic Analysis," Seventh Edition, First Printing 1999, 2 pages.
Urwin, Peter, et al., "Functional characterization of the EMCV IRES in plants," The Plant journal (2000) 24(5), 583-589, Jul. 25, 2000.

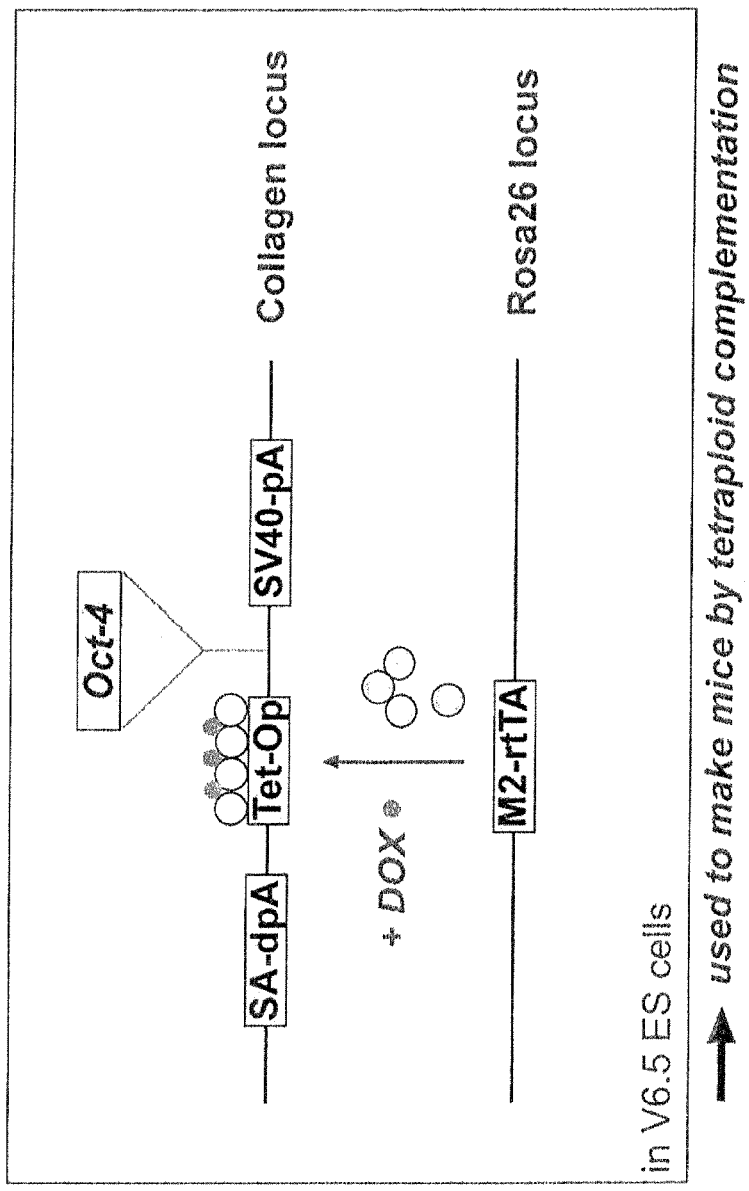
Figure 1. Inducible Oct4 allele

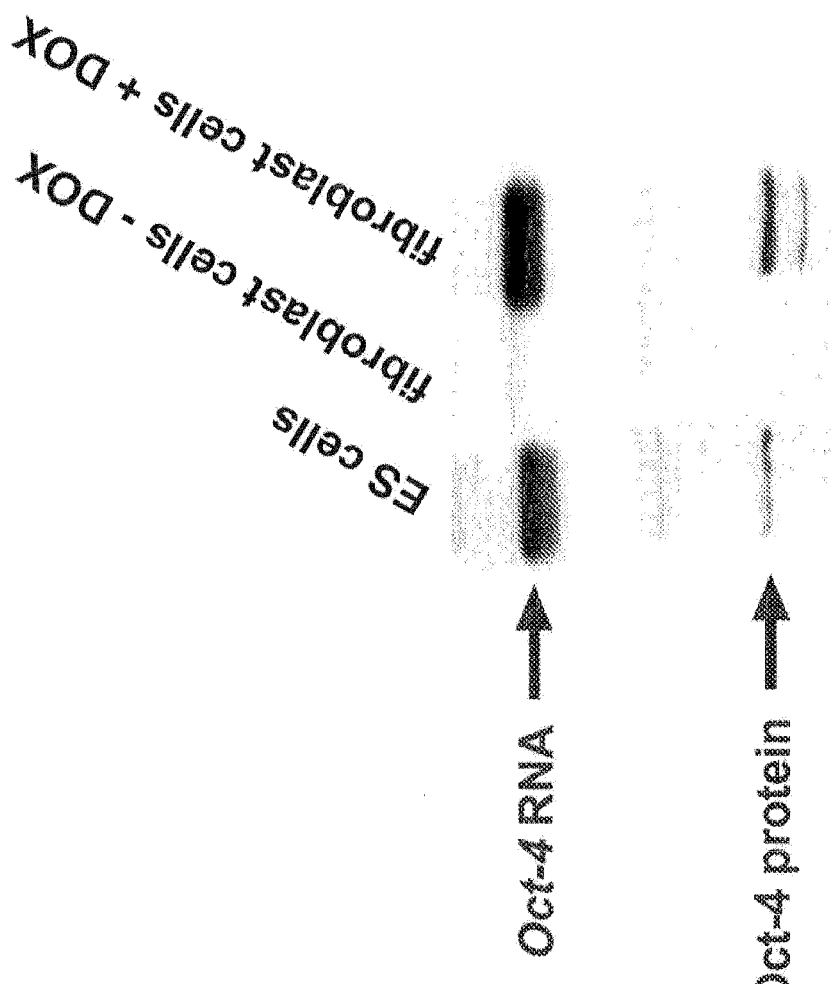

METHODS FOR REPROGRAMMING SOMATIC CELLS

CROSS-REFERENCE TO RELATED APPLICATIONS

This application is a continuation of U.S. application Ser. No. 14/923,321, filed Oct. 26, 2015, which is a continuation of U.S. application Ser. No. 13/646,430, filed Oct. 5, 2012 (U.S. Pat. No. 9,169,490), which is a continuation of U.S. application Ser. No. 12/703,061, filed Feb. 9, 2010 (U.S. Pat. No. 8,940,536), which is a divisional of U.S. application Ser. No. 10/997,146, filed Nov. 24, 2004 (U.S. Pat. No. 7,682,828), which claims the benefit of U.S. Provisional Application No. 60/525,612, filed Nov. 26, 2003, and U.S. Provisional Application No. 60/530,042, filed Dec. 15, 2003, the specifications of which are incorporated herein by reference in their entirety.

GOVERNMENTAL FUNDING

This invention was made with government support under R37 CA84198 awarded by the National Institutes of Health. The government has certain rights in the invention.

BACKGROUND OF THE INVENTION

Pluripotent stem cells have the potential to differentiate into the full range of daughter cells having distinctly different morphological, cytological or functional phenotypes unique to a specific tissue. By contrast, descendants of pluripotent cells are restricted progressively in their differentiation potential, with some cells having only one fate. Pluripotent cells have extraordinary scientific and therapeutic potential, as they can be differentiated along the desired differentiation pathway in a precisely controlled manner and used in cell-based therapy.

Two categories of pluripotent stem cells are known to date: embryonic stem cells and embryonic germ cells. Embryonic stem cells are pluripotent stem cells that are derived directly from an embryo. Embryonic germ cells are pluripotent stem cells that are derived directly from the fetal tissue of aborted fetuses. For purposes of simplicity, embryonic stem cells and embryonic germ cells will be collectively referred to as "ES" cells herein.

ES cells are presently obtained via several methods. In a first method, an ES cell line is derived from the inner cell mass of a normal embryo in the blastocyst stage (See U.S. Pat. No. 6,200,806, Thompson, J. A. et al. Science, 282: 1145-7, 1998 and Hogan et al., 2003). A second method for creating pluripotent ES cells utilizes the technique of somatic cell nuclear transfer (SCNT). In this technique, the nucleus is removed from a normal egg, thus removing the genetic material. Next, a donor diploid somatic cell is placed next to the enucleated egg and the two cells are fused, or the nucleus is introduced directly into the oocyte by micromanipulation. The fused cell has the potential to develop into a viable embryo, which may then be sacrificed to remove that portion of the embryo containing the stem cell producing inner cell mass.

In a third method, the nucleus of a human cell is transplanted into an entirely enucleated animal oocyte of a species different from the donor cell (referred to herein as animal stem cell nuclear transfer, or "ASCNT"). See U.S. Pat. Application Ser. No. 20010012513 (2001). The resultant chimeric cells are used for the production of pluripotent ES cells, in particular human-like pluripotent ES cells. One disadvantage of this technique is that these chimeric cells may contain unknown non-human viruses and still contain the mitochondria of the animal species. Thus, there would be substantial risks of immune rejection if such cells were used in cell transplantation therapies.

In a fourth method, ES cells can be isolated from the primordial germ cells found in the genital ridges of post-implanted embryos.

As described above, all presently available methods depend on controversial sources—embryos (either created naturally or via cloning), fetal tissue and via the mixing of materials of multiple species. The controversy surrounding the sources for such cells, according to many leading scientists and public and private organizations including the NIH, has greatly compromised and slowed the study of such cells and their application.

There is thus a great demand for alternative methods of generating pluripotent cells.

SUMMARY OF THE INVENTION

The present invention provides engineered somatic cells, in which one or more endogenous pluripotency gene(s) is operably linked to a selectable marker in such a manner that the expression of the selectable marker substantially matches the expression of the endogenous pluripotency gene to which the marker is linked. The invention also provides transgenic mice containing these engineered somatic cells.

The present invention also provides methods for reprogramming somatic cells to a less differentiated state. In the methods, engineered somatic cells of the invention are treated with an agent. Cells that express the selectable marker are then selected, and assessed for pluripotency characteristics. The treatment with an agent may be contacting the cells with an agent which alters chromatin structure, or may be transfecting the cells with at least one pluripotency gene, or both.

The present invention further provides methods for identifying an agent that reprograms somatic cells to a less differentiated state. In the methods, the engineered somatic cells described above are contacted with a candidate agent. Cells that express the selectable marker are then selected, and assessed for pluripotency characteristics. The presence of at least a subset of pluripotency characteristics indicates that the agent is capable of reprogramming somatic cells to a less-differentiated state. The agents identified by the present invention can then by used to reprogram somatic cells by contacting somatic cells with the agents.

The present invention also provides methods for identifying a gene that causes the expression of at least one endogenous pluripotency gene in somatic cells. In the methods, the engineered somatic cells are transfected with a cDNA library prepared from a pluripotent cell, such as an ES cell. The cells that express the appropriate selectable marker are then selected, and the expression of the appropriate endogenous pluripotency gene is examined. The expression of an endogenous pluripotency gene indicates that the cDNA encodes a protein whose expression in the cell results in, directly or indirectly, expression of the endogenous pluripotency gene.

The present invention further provides methods for treating a condition in an individual in need of such treatment. In certain embodiments, somatic cells are obtained from the individual and reprogrammed by the methods of the invention under conditions suitable for the cells to develop into cells of a desired cell type. The reprogrammed cells of a desired cell type are then harvested and introduced into the individual to treat the condition. In certain further embodiments, the somatic cells obtained from the individual contains a mutation in one or more genes. In these instances, the methods are modified so that the somatic cells obtained from the individual are first treated to restore the one or more normal gene(s) to the cells such that the resulting cells carry the normal endogenous gene, which are then introduced into the individual. In certain other embodiments, methods of the invention can be used to treat individuals in need of a functional organ. In the methods, somatic cells are obtained from an individual in need of a functional organ, and reprogrammed by the methods of the invention to produce reprogrammed somatic cells. Such reprogrammed somatic cells are then cultured under conditions suitable for development of the reprogrammed somatic cells into a desired organ, which is then introduced into the individual. The methods are useful for treating any one of the following conditions: a neurological, endocrine, structural, skeletal, vascular, urinary, digestive, integumentary, blood, autoimmune, inflammatory, or muscular condition.

The present invention also provides methods for producing a cloned animal. In the methods, a somatic cell is isolated from an animal having desired characteristics, and reprogrammed using the methods of the invention to produce one or more reprogrammed pluripotent somatic cell ("RPSC"). The RPSCs are then inserted into a recipient embryo, and the resulting embryo is cultured to produce an embryo of suitable size for implantation into a recipient female, which is then transferred into a recipient female to produce a pregnant female. The pregnant female is maintained under conditions appropriate for carrying the embryo to term to produce chimeric animal progeny, which is then bred with a wild type animal to produce a cloned animal.

In certain embodiments, the RPSCs may alternatively be cryopreserved for future cloning uses. In certain other embodiments, genetic modification, such as a targeted mutation, may be introduced into the RPSCs prior to its insertion into a recipient embryo.

The present invention also provides methods for producing a cloned avian. In the methods, a somatic cell is isolated from an avian having desired characteristics, and reprogrammed using the methods of the invention to produce one or more reprogrammed pluripotent somatic cell ("RPSC"). The RPSCs are then inserted into eggs that are unable to develop into an embryo, and the resulting eggs are then incubated to produce avian offspring having the genotype of the RPSC, thereby producing a cloned avian.

It is contemplated that all embodiments described above are applicable to all different aspects of the invention. It is also contemplated that any of the above embodiments can be freely combined with one or more other such embodiments whenever appropriate.)

Specific embodiments of the invention are described in more detail below. However, these are illustrative embodiments, and should not be construed as limiting in any respect.

BRIEF DESCRIPTION OF THE DRAWINGS

FIG. 1 depicts an inducible Oct4 allele.
FIG. 2 shows the expression of the inducible Oct4 transgene by Northern blot and Western blot analysis.

DETAILED DESCRIPTION OF THE INVENTION

Overview

Presently, human ES cells or ES-like cells can only be generated from controversial sources. It would be useful to reprogram somatic cells directly into pluripotent cells. Nuclei from somatic cells retain the totopotency potential to direct development of an animal, as demonstrated by nuclear transfer technology. It would be useful to reprogram somatic cells directly into ES cells without the use of oocytes and nuclear transfer technology.

Applicants have devised novel methods of reprogramming somatic cells to generate pluripotent cells or multipotent cells. Applicants have also devised novel methods to identify agents that reprogram somatic cells. The methods take advantage of the engineered somatic cells designed by Applicants, in which an endogenous gene typically associated with pluripotency ("pluripotency gene") is engineered to be operably linked to a selectable marker in a manner that the expression the endogenous pluripotency gene substantially matches the expression of the selectable marker. Because pluripotency genes are generally expressed only in pluripotent cells and not in somatic cells, the expression of an endogenous pluripotent gene(s) is an indication of successful reprogramming. Having a selectable marker operably linked to an endogenous pluripotency gene gives one a powerful mechanism to select for potentially reprogrammed somatic cells, which likely is a rare occurrence. The resulting cells may be further assessed for pluripotency characteristics to confirm whether a somatic cell has been successfully reprogrammed to pluripotency.

Generating pluripotent or multipotent cells by somatic cell reprogramming using the methods of the present invention has at least two advantages. First, the methods of the present invention allow one to generate autologous pluripotent cells, which are cells specific to a patient. The use of autologous cells in cell therapy offers a major advantage over the use of non-autologous cells, which are likely to be subject to immunological rejection. In contrast, autologous cells are unlikely to elicit significant immunological responses (See Munsie et al, 2000). Second, the methods of the present invention allow one to generate pluipotent without using embryos, oocytes and/or nuclear transfer technology.

A pluripotent cell is a cell that has the potential to divide in vitro for a long period of time (greater than one year) and has the unique ability to differentiate into cells derived from all three embryonic germ layers—endoderm, mesoderm and ectoderm.

A multipotent cell is a cell that is able to differentiate into some but not all of the cells derived from all three germ layers. Thus, a multipotent cell is a partially differentiated cell. Adult stem cells are multipotent cells. Known adult stem cells include, for example, hematopoietic stem cells and neural stem cells. A hematopoietic stem cell is multipotent because it has the ability to differentiate into all types of specific blood cells, but it is unlikely that they can differentiate into all cells of a given animal or human. Multipotent/adult stem cells have a great deal of promise in research and in the area of therapeutic applications. For example, multipotent/adult stem cells have already been used in humans in attempts to treat certain blood, neural and cancer diseases.

The term "pluripotency gene", as used herein, refers to a gene that is associated with pluripotency. The expression of a pluripotency gene is typically restricted to pluripotent stem cells, and is crucial for the functional identity of pluripotent stem cells. The transcription factor Oct-4 (also called Pou5fl, Oct-3, Oct3/4) is an example of a pluripotency gene. Oct-4 has been shown to be required for establishing and maintaining the undifferentiated phenotype of ES cells and plays a major role in determining early events in embryogenesis and cellular-differentiation (Nichols et al., 1998, Cell 95:379-391; Niwa et al., 2000, Nature Genet. 24:372-376). Oct-4 is down-regulated as stem cells differentiate into specialised cells. Other exemplary pluripotency genes include Nanog, and Stella (See Chambers et al., 2003, Cell 113: 643-655; Mitsui et al., Cell. 2003, 113(5):631-42; Bortvin et al. Development. 2003, 130(8):1673-80; Saitou et al., Nature. 2002, 418 (6895):293-300.

Engineered Somatic Cells and Transgenic Mice Comprising Such Cells

The present invention provides somatic cells comprising an endogenous pluripotency gene linked to DNA encoding a selectable marker in such a manner that the expression of the selectable marker substantially matches the expression of the endogenous pluripotency gene. In one embodiment, the somatic cells of the present invention comprise a first endogenous pluripotency gene linked to DNA encoding a first selectable marker in such a manner that the expression of the first selectable marker substantially matches the expression of the first endogenous pluripotency gene. The somatic cells may also be engineered to comprise any number of endogenous pluripotency genes respectively linked to a distinct selectable marker. Thus, in another embodiment, the somatic cells of the present invention comprise two endogenous pluripotency genes, each of which is linked to DNA encoding a distinct selectable marker. In a further embodiment, the somatic cells of the present invention comprise three endogenous pluripotency genes, each of which is linked to DNA encoding a distinct selectable marker. The somatic cells described above will be collectively referred in this application as "engineered somatic cells." The engineered somatic cells may be further engineered to have one or more pluripotency gene expressed as a transgene under an inducible promoter.

The selectable marker is linked to an appropriate endogenous pluripotency gene such that the expression of the selectable marker substantially matches the expression of the endogenous pluripotency gene. By "substantially match", it is meant that the expression of the selectable marker substantially reflects the expression pattern of the endogenous pluripotency gene. In other words, the selectable marker and the endogenous pluripotency gene are co-expressed. For purpose of the present invention, it is not necessary that the expression level of the endogenous gene and the selectable marker is the same or even similar. It is only necessary that the cells in which an endogenous pluripotency gene is activated will also express the selectable marker at a level sufficient to confer a selectable phenotype on the reprogrammed cells. For example, when the selectable marker is a marker that confers resistance to a lethal drug (a "drug resistance marker"), the cells are engineered in a way that allows cells in which an endogeneous pluripotency gene is activated to also express the drug resistance marker at a sufficient level to confer on reprogrammed cells resistance to lethal drugs. Thus, reprogrammed cells will survive and proliferate whereas non-reprogrammed cells will die.

The DNA encoding a selectable marker may be inserted downstream from the end of the open reading frame (ORF) encoding the desired endogenous pluripotency gene, anywhere between the last nucleotide of the ORF and the first nucleotide of the polyadenylation site. An internal ribosome entry site (IRES) may be placed in front of the DNA encoding the selectable marker. Alternatively, the DNA encoding a selectable marker may be inserted anywhere within the ORF of the desired endogenous pluripotency gene, downstream of the promoter, with a termination signal. An internal ribosome entry site (IRES) may be placed in front of the DNA encoding the selectable marker. The selectable marker may be inserted into only one allele, or both alleles, of the endogenous pluripotency gene.

The somatic cells in the invention may be primary cells or immortalized cells. Such cells may be primary cells (non-immortalized cells), such as those freshly isolated from an animal, or may be derived from a cell line (immortalized cells).

The somatic cells in the present invention are mammalian cells, such as, for example, human cells or mouse cells. They may be obtained by well-known methods, from different organs, e.g., skin, lung, pancreas, liver, stomach, intestine, heart, reproductive organs, bladder, kidney, urethra and other urinary organs, etc., generally from any organ or tissue containing live somatic cells. Mammalian somatic cells useful in the present invention include, by way of example, adult stem cells, sertoli cells, endothelial cells, granulosa epithelial, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells, etc. generally any live somatic cells. The term "somatic cells", as used herein, also includes adult stem cells. An adult stem cell is a cell that is capable of giving rise to all cell types of a particular tissue. Exemplary adult stem cells include hematopoietic stem cells, neural stem cells, and mesenchymal stem cells.

In one embodiment, the engineered somatic cells are obtained from a transgenic mouse comprising such engineered somatic cells. Such transgenic mouse can be produced using standard techniques known in the art. For example, Bronson et al. describe a technique for inserting a single copy of a transgene into a chosen chromosomal site. See Bronson et al., 1996. Briefly, a vector containing the desired integration construct (for example, a construct containing a selectable marker linked to a pluripotency gene) is introduced into ES cells by standard techniques known in the art. The resulting ES cells are screened for the desired integration event, in which the knock-in vector is integrated into the desired endogenous pluripotency gene locus such that the selectable marker is integrated into the genomic locus of the pluripotency gene and is under the control of the pluripotency gene promoter. The desired ES cell is then used to produce transgenic mouse in which all cell types contain the correct integration event. Desired types of cells may be selectively obtained from the transgenic mouse and maintained in vitro. In one embodiment, two or more transgenic mice may be created, each carrying a distinct integration construct. These mice may then be bred to generate mice that carry multiple desired integration construct. For example, one type of transgenic mouse may be created to carry an endogenous pluripotency gene linked to a selectable marker, while a second type of transgenic mouse may be created to carry a pluripotency gene expressed as a transgene under an inducible promoter. These two types of mice may then be bred to generate transgenic mice that have both a selectable marker linked to an endogenous pluripotency gene and an additional pluripotency gene expressed as a transgene under an inducible promoter. These two pluripotency genes may or may not be the same. Many variables are contemplated: the identity of the endogenous pluripotency gene linked to marker, the identity of the pluripotency gene expressed as a transgene, and the number of the endogenous pluripotency gene linked to a selectable marker, and the number of pluripotency gene expressed as a transgene. The present invention encompasses all possible combinations of these variables.

Alternatively, engineered somatic cells of the present invention may be produced by direct introduction of the desired construct into somatic cells. DNA construct may be introduced into cells by any standard technique known in the art, such as viral transfection (eg. using an adenoviral system) or liposome-mediated transfection. Any means known in the art to generate somatic cells with targeted integration can be used to produce somatic cells of the invention. In mammalian cells, homologous recombination occurs at much lower frequency compared to non-homologous recombination. To facilitate the selection of homologous recombination events over the non-homologous recombination events, at least two enrichment methods have been developed: the positive-negative selection (PNS) method and the "promoterless" selection method (Sedivy and Dutriaux, 1999). Briefly, PNS, the first method, is in genetic terms a negative selection: it selects against recombination at the incorrect (non-homologous) loci by relying on the use of a negatively selectable gene that is placed on the flanks of a targeting vector. On the other hand, the second method, the "promoterless" selection, is a positive selection in genetic terms: it selects for recombination at the correct (homologous) locus by relying on the use of a positively selectable gene whose expression is made conditional on recombination at the homologous target site. The disclosure of Sedivy and Dutriaux is incorporated herein.

A selectable marker, as used herein, is a marker that, when expressed, confers upon recipient cells a selectable phenotype, such as antibiotic resistance, resistance to a cytotoxic agent, nutritional prototrophy or expression of a surface protein. The presence of a selectable marker linked to an endogenous pluripotency gene makes it possible to identify and select reprogrammed cells in which the endogenous pluripotency gene is expressed. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), and hisD gene.

The present invention further provides transgenic mice comprising the somatic cells of the invention.

Methods for Reprogramming Somatic Cells

The present invention further provides methods for reprogramming somatic cells to a less differentiated state. The resulting cells are termed "reprogrammed somatic cells" ("RSC") herein. A RSC may be a reprogrammed pluripotent somatic cell ("RPSC"), a reprogrammed multipotent somatic cell ("RMSC"), or a reprogrammed somatic cell of varying differentiation status.

In general, the methods comprise treating the engineered somatic cells with an agent. The treatment with an agent may be contacting the cells with an agent which alters chromatin structure, or may be transfecting the cells with one or more pluripotency gene, or both. The above two treatments may be concurrent, or may be sequential, with no particular preference for order. In a further embodiment, reprogrammed somatic cells are identified by selecting for cells that express the appropriate selectable marker. In still a further embodiment, reprogrammed somatic cells are further assessed for pluripotency characteristics. The presence of pluripotency characteristics indicates that the somatic cells have been reprogrammed to a pluripotent state.

Differentiation status of cells is a continuous spectrum, with terminally differentiated state at one end of this spectrum and de-differentiated state (pluripotent state) at the other end. Reprogramming, as used herein, refers to a process that alters or reverses the differentiation status of a somatic cell, which can be either partially or terminally differentiated. Reprogramming includes complete reversion, as well as partial reversion, of the differentiation status of a somatic cell. In other words, the term "reprogramming", as used herein, encompasses any movement of the differentiation status of a cell along the spectrum toward a less-differentiated state. For example, reprogramming includes reversing a multipotent cell back to a pluripotent cell, reversing a terminally differentiated cell back to either a multipotent cell or a pluripotent cell. In one embodiment, reprogramming of a somatic cell turns the somatic cell all the way back to a pluripotent state. In another embodiment, reprogramming of a somatic cell turns the somatic cell back to a multipotent state. The term "less-differentiated state", as used herein, is thus a relative term and includes a completely de-differentiated state and a partially differentiated state.

The term "pluripotency characteristics", as used herein, refers to many characteristics associated with pluripotency, including, for example, the ability to differentiate into all types of cells and an expression pattern distinct for a pluripotent cell, including expression of pluripotency genes, expression of other ES cell markers, and on a global level, a distinct expression profile known as "stem cell molecular signature" or "stemness."

Thus, to assess reprogrammed somatic cells for pluripotency characteristics, one may analyze such cells for different growth characteristics and ES cell-like morphology. Cells may be injected subcutaneously into immunocompromised SCID mice to induce teratomas (a standard assay for ES cells). ES-like cells can be differentiated into embryoid bodies (another ES specific feature). Moreover, ES-like cells can be differentiated in vitro by adding certain growth factors known to drive differentiation into specific cell types. Self-renewing capacity, marked by induction of telomerase activity, is another plutipotency characteristics that can be monitored. One may carry out functional assays of the reprogrammed somatic cells by introducing them into blastocysts and determine whether the cells are capable of giving rise to all cell types. See Hogan et al., 2003. If the reprogrammed cells are capable of forming a few cell types of the body, they are multipotent; if the reprogrammed cells are capable of forming all cell types of the body including germ cells, they are pluripotent.

One may also examine the expression of an individual pluripotency gene in the reprogrammed somatic cells to assess their pluripotency characteristics. Additionally, one may assess the expression of other ES cell markers. Stage-specific embryonic 1 5 antigens-1, -3, and -4 (SSEA-1, SSEA-3, SSEA-4) are glycoproteins specifically expressed in early embryonic development and are markers for ES cells (Solter and Knowles, 1978, Proc. Natl. Acad. Sci. USA 75:5565-5569; Kannagi et al., 1983, EMBO J 2:2355-2361). Elevated expression of the enzyme Alkaline Phosphatase (AP) is another marker associated with undifferentiated embryonic stem cells (Wobus et al., 1984, Exp. Cell 152: 212-219; Pease et al., 1990, Dev. Biol. 141:322-352). Other stem/progenitor cells markers include the intermediate neurofilament nestin (Lendahl et al., 1990, Cell 60:585-595; Dah-Istrand et al., 1992, J. Cell Sci. 103:589-597), the membrane glycoprotein prominin/AC133 (Weigmann et al., 1997, Proc. Natl. Acad. USA 94:12425-12430; Corbeil et al., 1998, Blood 91:2625-

22626), the transcription factor Tcf-4 (Korinek et al, 1998, Nat. Genet. 19: 379-383; Lee et al., 1999, J. Biol. Chem. 274.1 566-1 572), and the transcription factor Cdx1 (Duprey et al., 1988, Genes Dev. 2:1647-1654; Subramania'n et al., 1998, Differentiation 64:11-1 8).

One may additionally conduct expression profiling of the reprogrammed somatic cells to assess their pluripotency characteristics. Pluripotent cells, such as embryonic stem cells, and multipotent cells, such as adult stem cells, are known to have a distinct pattern of global gene expression profile. This distinct pattern is termed "stem cell molecular signature", or "stemness". See, for example, Ramalho-Santos et al., Science 298: 597-600 (2002); Ivanova et al., Science 298: 601-604.

Somatic cells may be reprogrammed to gain either a complete set of the pluripotency characteristics and are thus pluripotent. Alternatively, somatic cells may be reprogrammed to gain only a subset of the pluripotency characteristics. In another alternative, somatic cells may be reprogrammed to be multipotent.

In a further embodiment, in conjunction with contacting the somatic cells of the invention with an agent which alters chromatin structure, at least one gene that affects pluripotent state of a cell may be further introduced into the same cells. This may be carried out sequentially. For example, the somatic cells of the invention may be first contacted with an agent which alters chromatin structure. Then at least one pluripotency gene can be introduced into the same cells, or vice versa. Alternatively, the two steps may be carried out simultaneously.

Genes that affect pluripotent state of a cell includes pluripotency genes, genes involved in chromatin remodeling, and genes that are important for maintaining pluripotency, such as LIF, BMP, and PD098059 (See Cell, 115: 281-292 (2003); Philos Trans R Soc Lond B Biol Sci. 2003 Aug. 29; 358(1436):1397-402).

The exogenously introduced pluripotency gene may be carried out in several ways. In one embodiment, the exogenously introduced pluripotency gene may be expressed from a chromosomal locus different from the endogenous chromosomal locus of the pluripotency gene. Such chromosomal locus may be a locus with open chromatin structure, and contain gene(s) dispensible for a somatic cell. In other words, the desirable chromosomal locus contains gene(s) whose disruption will not cause cells to die. Exemplary chromosomal loci include, for example, the mouse ROSA 26 locus and type II collagen (Col2a1) locus (See Zambrowicz et al., 1997) The exogenously introduced pluripotency gene may be expressed from an inducible promoter such that their expression can be regulated as desired.

In an alternative embodiment, the exogenously introduced pluripotency gene may be transiently transfected into cells, either individually or as part of a cDNA expression library, prepared from pluripotent cells. Such pluripotent cells may be embryonic stem cells, oocytes, blastomeres, inner cell mass cells, embryonic germ cells, embryoid body (embryonic) cells, morula-derived cells, teratoma (teratocarcinoma) cells, and multipotent partially differentiated embryonic stem cells taken from later in the embryonic development process.

The cDNA library is prepared by conventional techniques. Briefly, mRNA is isolated from an organism of interest. An RNA-directed DNA polymerase is employed for first strand synthesis using the mRNA as template. Second strand synthesis is carried out using a DNA-directed DNA polymerase which results in the cDNA product. Following conventional processing to facilitate cloning of the cDNA, the cDNA is inserted into an expression vector such that the cDNA is operably linked to at least one regulatory sequence. The choice of expression vectors for use in connection with the cDNA library is not limited to a particular vector. Any expression vector suitable for use in mouse cells is appropriate. In one embodiment, the promoter which drives expression from the cDNA expression construct is an inducible promoter. The term regulatory sequence includes promoters, enhancers and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express cDNAs. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

The exogenously introduced pluripotency gene may be expressed from an inducible promoter. The term "inducible promoter", as used herein, refers to a promoter that, in the absence of an inducer (such as a chemical and/or biological agent), does not direct expression, or directs low levels of expression of an operably linked gene (including cDNA), and, in response to an inducer, its ability to direct expression is enhanced. Exemplary inducible promoters include, for example, promoters that respond to heavy metals (CRC Boca Raton, Fla. (1991), 167-220; Brinster et al. Nature (1982), 296, 39-42), to thermal shocks, to hormones (Lee et al. P.N.A.S. USA (1988), 85, 1204-1208; (1981), 294, 228-232; Klock et al. Nature (1987), 329, 734-736; Israel and Kaufman, Nucleic Acids Res. (1989), 17, 2589-2604), promoters that respond to chemical agents, such as glucose, lactose, galactose or antibiotic.

A tetracycline-inducible promoter is an example of an inducible promoter that responds to an antibiotics. See Gossen et al., 2003. The tetracycline-inducible promoter comprises a minimal promoter linked operably to one or more tetracycline operator(s). The presence of tetracycline or one of its analogues leads to the binding of a transcription activator to the tetracycline operator sequences, which activates the minimal promoter and hence the transcription of the associated cDNA. Tetracycline analogue includes any compound that displays structural homologies with tetracycline and is capable of activating a tetracycline-inducible promoter. Exemplary tetracycline analogues includes, for example, doxycycline, chlorotetracycline and anhydrotetracycline.

Thus, in one embodiment, the present invention provides mice and somatic cells carrying at least one pluripotency gene expressed as a transgene under an inducible promoter. It is possible that somatic cells with such inducible pluripotency transgene(s) are more prone to be reprogrammed.

Any of the engineered somatic cells of the present invention may be used in the methods. In one embodiment, somatic cells used in the methods comprise only one endogenous pluripotency gene linked to a first selectable marker, and the selection step is carried out to select for the expression of the first selectable marker. In an alternative embodiment, the somatic cells used in the methods comprise any number of endogenous pluripotency genes, each of which is linked to a distinct selectable marker respectively, and the selection step is carried out to select for at least a subset of the selectable markers. For example, the selection step may be carried out to select for all the selectable markers linked to the various endogenous pluripotency genes.

In an alternative embodiment, somatic cells used in the method comprise a selectable marker linked to an endogenous pluripotency gene and an additional pluripotency gene expressed as a transgene under an inducible promoter. For these cells, the method of reprogramming may comprises induce the expression of the pluripotency transgene and select for the expression of the selectable marker. The method may further comprise contacting the somatic cells with an agent that alter chromatic structure.

Without wishing to be bound by theory, the agents used in the method may cause chromatin to take on a more open structure, which is more permissive for gene expression. DNA methylation and histone acetylation are two known events that alter chromatin toward a more closed structure. For example, loss of methylation by genetic deletion of DNA methylation enzyme Dnmt1 in fibroblasts results in reactivation of endogenous Oct4 gene. See J. Biol. Chem. 277: 34521-30, 2002; and Bergman and Mostoslaysky, Biol. Chem. 1990. Thus, DNA methylation inhibitors and histone deacelyation inhibitors are two classes of agents that may be used in the methods of the invention. Exemplary agents include 5-aza-cytidine, TSA and valproic acid.

In another embodiment, methods of the invention may further include repeating the steps of treating the cells with an agent. The agent used in the repeating treatment may be the same as, or different from, the one used during the first treatment.

Methods for Screening for an Agent that Reprograms Somatic Cells

The present invention also provides methods for identifying an agent that reprograms somatic cells to a less-differentiated state, as well as the agents thus identified. In one embodiment, the methods comprise contacting the engineered somatic cells of the invention with a candidate agent, selecting for cells that express the appropriate selectable marker. The presence of cells that express the appropriate selectable marker indicates that the agent reprograms somatic cells. Such an agent is referred as a "reprogramming agent" for purpose of this application.

In a further embodiment, the methods comprise contacting the engineered somatic cells of the invention with a candidate agent, selecting for cells that express the appropriate selectable marker, and assessing the cells so selected for pluripotency characteristics. The presence of a complete set of pluripotency characteristics indicates that the agent reprograms somatic cells to become pluripotent.

Candidate agents used in the invention encompass numerous chemical classes, though typically they are organic molecules, including small organic compounds. Candidate agents are also found among biomolecules including peptides, saccharides, fatty acids, steroids, purines, pyrimidines, nucleic acids and derivatives, structural analogs or combinations thereof.

Candidate agents may be naturally arising, recombinant or designed in the laboratory. The candidate agents may be isolated from microorganisms, animals, or plants, or may be produced recombinantly, or synthesized by chemical methods known in the art. In some embodiments, candidate agents are isolated from libraries of synthetic or natural compounds using the methods of the present invention. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, including acylation, alkylation, esterification, amidification, to produce structural analogs.

There are numerous commercially available compound libraries, including, for example, the Chembridge DIVER-Set. Libraries are also available from academic investigators, such as the Diversity set from the NCI developmental therapeutics program.

The screening methods mentioned above are based on assays performed on cells. These cell-based assays may be performed in a high throughput screening (HTS) format, which has been described in the art. For example, Stockwell et al. described a high-throughput screening of small molecules in miniaturized mammalian cell-based assays involving post-translational modifications (Stockwell et al., 1999). Likewise, Qian et al. described a leukemia cell-based assay for high-throughput screening for anti-cancer agents (Qian et al., 2001). Both references are incorporated herein in their entirety.

A reprogramming agent may belong to any one of many different categories. For example, a reprogramming agent may be a chromatin remodeling agent. A chromatin remodeling agent may be a protein involved in chromatin remodeling or an agent known to alter chromatin toward a more open structure, such as a DNA methylation inhibitor or a histone deacelyation inhibitor. Exemplary compounds include 5-aza-cytidine, TSA and valproic acid. For another example, such an agent may be a pluripotency protein, including, for example, Nanog, Oct-4 and Stella. Such an agent may also be a gene essential for pluripotency, including, for example, Sox2, FoxD3, and LIF, and Stat3. See Smith et al. 1988, William et al., 1988, Ihle, 1996, Avilion et al., 2003, and Hanna et al., 2002)

Methods for Reprogramming Somatic Cells with a Reprogramming Agent

The reprogramming agent identified by the methods of the present invention is useful for reprogramming somatic cells into pluripotent or multipotent cells. Accordingly, the present invention provides methods for reprogramming somatic cells to a less differentiated state, comprising contacting somatic cells with a reprogramming agent. The somatic cells used may be native somatic cells, or engineered somatic cells. It is not necessary for these cells to carry a selectable marker integrated into the endogenous locus of a pluripotency gene.

Reprogrammed Somatic Cells and these Uses

The present invention also provides reprogrammed somatic cells (RSCs), including reprogrammed pluripotent somatic cells (RPSCs), produced by the methods of the invention. These methods, useful for the generation of cells of a desired cell type, have wide range of applications. For one example, these methods have applications in livestock management, involving the precise genetic manipulation of animals for economic or health purposes. For another example, these methods have medical application in treating or preventing a condition.

Accordingly, the invention provides methods for the treatment or prevention of a condition in a mammal. In one embodiment, the methods start with obtaining somatic cells from the individual, reprogramming the somatic cells so obtained by methods of the present invention to obtain RPSCs. The RPSCs are then cultured under conditions suitable for development of the RPSCs into cells of a desired cell type. The developed cells of the desired cell type are harvested and introduced into the individual to treat the condition. In an alternative embodiment, the methods start with obtaining somatic cells from the individual, reprogramming the somatic cells so obtained by methods of the present invention. The RPSCs are then cultured under conditions suitable for development of the RPSCs into a desired organ, which is harvested and introduced into the individual to treat the condition.

The RPSCs of the present invention are ES-like cells, and thus may be induced to differentiate to obtain the desired cell types according to known methods to differentiate ES cells. For example, the RPSCs may be induced to differentiate into hematopoietic stem cells, muscle cells, cardiac muscle cells, liver cells, cartilage cells, epithelial cells, urinary tract cells, etc., by culturing such cells in differentiation medium and under conditions which provide for cell differentiation. Medium and methods which result in the differentiation of embryonic stem cells are known in the art as are suitable culturing conditions.

For example, Palacios et al., Proc. Natl. Acad. Sci., USA, 92: 7530-37 (1995) teaches the production of hematopoietic stem cells from an embryonic cell line by subjecting stem cells to an induction procedure comprising initially culturing aggregates of such cells in a suspension culture medium lacking retinoic acid followed by culturing in the same medium containing retinoic acid, followed by transferal of cell aggregates to a substrate which provides for cell attachment.

Moreover, Pedersen, J. Reprod. Fertil. Dev., 6: 543-52 (1994) is a review article which references numerous articles disclosing methods for in vitro differentiation of embryonic stem cells to produce various differentiated cell types including hematopoietic cells, muscle, cardiac muscle, nerve cells, among others.

Further, Bain et al., Dev. Biol., 168:342-357 (1995) teaches in vitro differentiation of embryonic stem cells to produce neural cells which possess neuronal properties. These references are exemplary of reported methods for obtaining differentiated cells from embryonic or stem-like cells. These references and in particular the disclosures therein relating to methods for differentiating embryonic stem cells are incorporated by reference in their entirety herein.

Thus, using known methods and culture medium, one skilled in the art may culture the subject embryonic or stem-like cells to obtain desired differentiated cell types, e.g., neural cells, muscle cells, hematopoietic cells, etc. In addition, the use of inducible Bcl-2 or Bcl-x1 might be useful for enhancing in vitro development of specific cell lineages. In vivo, Bcl-2 prevents many, but not all, forms of apoptotic cell death that occur during lymphoid and neural development. A thorough discussion of how Bcl-2 expression might be used to inhibit apoptosis of relevant cell lineages following transfection of donor cells is disclosed in U.S. Pat. No. 5,646,008, which is herein incorporated by reference.

The subject RPSCs may be used to obtain any desired differentiated cell type. Therapeutic usages of such differentiated human cells are unparalleled. For example, human hematopoietic stem cells may be used in medical treatments requiring bone marrow transplantation. Such procedures are used to treat many diseases, e.g., late stage cancers such as ovarian cancer and leukemia, as well as diseases that compromise the immune system, such as AIDS. Hematopoietic stem cells can be obtained, e.g., by fusing adult somatic cells of a cancer or AIDS patient, e.g., epithelial cells or lymphocytes with an enucleated oocyte, e.g., bovine oocyte, obtaining embryonic or stem-like cells as described above, and culturing such cells under conditions which favor differentiation, until hematopoietic stem cells are obtained. Such hematopoietic cells may be used in the treatment of diseases including cancer and AIDS.

The methods of the present invention can also be used to treat, prevent, or stabilize a neurological disease such as Alzheimer's disease, Parkinson's disease, Huntington's disease, or ALS, lysosomal storage diseases, multiple sclerosis, or a spinal cord injury. For example, somatic cells may be obtained from the individual in need of treatment, and reprogrammed to gain pluripotency, and cultured to derive neurectoderm cells that may be used to replace or assist the normal function of diseased or damaged tissue.

For the treatment or prevention of endocrine conditions, RPSCs that produce a hormone, such as a growth factor, thyroid hormone, thyroid-stimulating hormone, parathyroid hormone, steroid, serotonin, epinephrine, or norepinephrine may be administered to a mammal. Additionally, reprogrammed epithelial cells may be administered to repair damage to the lining of a body cavity or organ, such as a lung, gut, exocrine gland, or urogenital tract. It is also contemplated that RPSCs may be administered to a mammal to treat damage or deficiency of cells in an organ such as the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, or uterus.

The great advantage of the present invention is that it provides an essentially limitless supply of isogenic or synegenic human cells suitable for transplantation. Therefore, it will obviate the significant problem associated with current transplantation methods, i.e., rejection of the transplanted tissue which may occur because of host versus graft or graft versus host rejection. Conventionally, rejection is prevented or reduced by the administration of anti-rejection drugs such as cyclosporin. However, such drugs have significant adverse side-effects, e.g., immunosuppression, carcinogenic properties, as well as being very expensive. The present invention should eliminate, or at least greatly reduce, the need for anti-rejection drugs, such as cyclosporine, imulan, FK-506, glucocorticoids, and rapamycin, and derivatives thereof.

RPSCs may also be combined with a matrix to form a tissue or organ in vitro or in vivo that may be used to repair or replace a tissue or organ in a recipient mammal. For example, RPSCs may be cultured in vitro in the presence of a matrix to produce a tissue or organ of the urogenital system, such as the bladder, clitoris, corpus cavernosum, kidney, testis, ureter, uretal valve, or urethra, which may then be transplanted into a mammal (Atala, Curr. Opin. Urol. 9(6):517-526, 1999). In another transplant application, synthetic blood vessels are formed in vitro by culturing reprogrammed cells in the presence of an appropriate matrix, and then the vessels are transplanted into a mammal for the treatment or prevention of a cardiovascular or circulatory condition. For the generation of donor cartilage or bone tissue, RPSCs such as chondrocytes or osteocytes are cultured in vitro in the presence of a matrix under conditions that allow the formation of cartilage or bone, and then the matrix containing the donor tissue is administered to a mammal. Alternatively, a mixture of the cells and a matrix may be administered to a mammal for the formation of the desired tissue in vivo. Preferably, the cells are attached to the surface of the matrix or encapsulated by the matrix. Examples of matrices that may be used for the formation of donor tissues or organs include collagen matrices, carbon fibers, polyvinyl alcohol sponges, acrylateamide sponges, fibrin-thrombin gels, hyaluronic acid-based polymers, and synthetic polymer matrices containing polyanhydride, polyorthoester, polyglycolic acid, or a combination thereof (see, for example, U.S. Pat. Nos. 4,846,835; 4,642,120; 5,786,217; and 5,041,138).

The RPSCs produced according to the invention may be used to produce genetically engineered or transgenic differentiated cells. Essentially, this will be effected by introducing a desired gene or genes, or removing all or part of an endogenous gene or genes of RPSCs produced according to the invention, and allowing such cells to differentiate into the desired cell type. A preferred method for achieving such modification is by homologous recombination because such technique can be used to insert, delete or modify a gene or genes at a specific site or sites in the stem-like cell genome.

This methodology can be used to replace defective genes, e.g., defective immune system genes, cystic fibrosis genes, or to introduce genes which result in the expression of therapeutically beneficial proteins such as growth factors, lymphokines, cytokines, enzymes, etc. For example, the gene encoding brain derived growth factor maybe introduced into human embryonic or stem-like cells, the cells differentiated into neural cells and the cells transplanted into a Parkinson's patient to retard the loss of neural cells during such disease. Examples of mutations that may be rescued using these methods include mutations in the cystic fibrosis gene; mutations associated with Dunningan's disease such as the R482W, R482Q, and R584H mutations in the lamin A gene; and mutations associated with the autosomal-dominant form of Emery Deyfuss muscular dystrophy such as the R249Q, R453W, and Q6STOP mutations in the lamin A gene. In the Q6STOP mutation, the codon for Gln6 is mutated to a stop codon.

Previously, cell types transfected with BDNF varied from primary cells to immortalized cell lines, either neural or non-neural (myoblast and fibroblast) derived cells. For example, astrocytes have been transfected with BDNF gene using retroviral vectors, and the cells grafted into a rat model of Parkinson's disease (Yoshimoto et al., Brain Research, 691:25-36, (1995)). This ex vivo therapy reduced Parkinson's-like symptoms in the rats up to 45% 32 days after transfer. Also, the tyrosine hydroxylase gene has been placed into astrocytes with similar results (Lundberg et al., Develop. Neurol., 139:39-53 (1996) and references cited therein).

However, such ex vivo systems have problems. In particular, retroviral vectors currently used are down-regulated in vivo and the transgene is only transiently expressed (review by Mulligan, Science, 260: 926-932 (1993)). Also, such studies used primary cells, astrocytes, which have finite life span and replicate slowly. Such properties adversely affect the rate of transfection and impede selection of stably transfected cells. Moreover, it is almost impossible to propagate a large population of gene targeted primary cells to be used in homologous recombination techniques.

By contrast, the difficulties associated with retroviral systems should be eliminated by the use of RPSCs of the present invention, which are ES-like cells. Using known methods to introduced desired genes/mutations into ES cells, RPSCs may be genetically engineered, and the resulting engineered cells differentiated into desired cell types, e.g., heniatopoietic cells, neural cells, pancreatic cells, cartilage cells, etc. Genes which may be introduced into the RPSCs include, for example, epidermal growth factor, basic fibroblast growth factor, glial derived neurotrophic growth factor, insulin-like growth factor (I and II), neurotrophin3, neurotrophin-4/5, ciliary neurotrophic factor, AFT-1, cytokine genes (interleukins, interferons, colony stimulating factors, tumor necrosis factors (alpha and beta), etc.), genes encoding therapeutic enzymes, collagen, human serum albumin, etc.

In addition, it is also possible to use one of the negative selection systems now known in the art for eliminating therapeutic cells from a patient if necessary. For example, donor cells transfected with the thymidine kinase (TK) gene will lead to the production of embryonic cells containing the TK gene. Differentiation of these cells will lead to the isolation of therapeutic cells of interest which also express the TK gene. Such cells may be selectively eliminated at any time from a patient upon gancyclovir administration. Such a negative selection system is described in U.S. Pat. No. 5,698,446, and is herein incorporated by reference.

Examples of diseases, disorders, or conditions that may be treated or prevented include neurological, endocrine, structural, skeletal, vascular, urinary, digestive, integumentary, blood, immune, auto-immune, inflammatory, endocrine, kidney, bladder, cardiovascular, cancer, circulatory, digestive, hematopoeitic, and muscular diseases, disorders, and conditions. In addition, reprogrammed cells may be used for reconstructive applications, such as for repairing or replacing tissues or organs.

With respect to the therapeutic methods of the invention, it is not intended that the administration of RPSCs to a mammal be limited to a particular mode of administration, dosage, or frequency of dosing; the present invention contemplates all modes of administration, including intramuscular, intravenous, intraarticular, intralesional, subcutaneous, or any other route sufficient to provide a dose adequate to prevent or treat a disease. The RPSCs may be administered to the mammal in a single dose or multiple doses. When multiple doses are administered, the doses may be separated from one another by, for example, one week, one month, one year, or ten years. One or more growth factors, hormones, interleukins, cytokines, or other cells may also be administered before, during, or after administration of the cells to further bias them towards a particular cell type.

The RPSCs of the present invention may be used as an in vitro model of differentiation, in particular for the study of genes which are involved in the regulation of early development. Differentiated cell tissues and organs using the RPSCs may be used in drug studies.

Furthermore, the RPSCs produced according to the invention maybe introduced into animals, e.g., SCID mice, cows, pigs, e.g., under the renal capsule or intramuscularly and used to produce a teratoma therein. This teratoma can be used to derive different tissue types. Also, the inner cell mass produced by X-species nuclear transfer may be introduced together with a biodegradable, biocompatible polymer matrix that provides for the formation of 3-dimensional tissues. After tissue formation, the polymer degrades, ideally just leaving the donor tissue, e.g., cardiac, pancreatic, neural, lung, liver. In some instances, it may be advantageous to include growth factors and proteins that promote angiogenesis. Alternatively, the formation of tissues can be effected totally in vitro, with appropriate culture media and conditions, growth factors, and biodegradable polymer matrices.

Applications of the Somatic Cell Reprogramming Methods and RPSCs in Animals

The reprogramming methods disclosed herein may be used to generate RPSCs for a variety of animal species. The RPSCs generated can be useful to produce desired animals. Animals include, for example, avians and mammals as well as any animal that is an endangered species. Exemplary birds include domesticated birds (e.g., quail, chickens, ducks, geese, turkeys, and guinea hens) as well as other birds such as birds of prey (e.g., hawks, falcons, ospreys, condors, etc.), endangered birds (e.g., parrots, California condor, etc.), ostriches etc. Exemplary mammals include murine, caprine, ovine, bovine, porcine, canine, feline and primate. Of these, preferred members include domesticated animals, including, for examples, cattle, buffalo, pigs, horses, cows, rabbits, guinea pigs, sheep, and goats.

RPSCs generated by the reprogramming methods of the present invention allows one, for the first time, to genetically engineer animals other than mouse and human. RPSCs are ES-like cells, and are thus amenable to genetic manipulation. To date, no ES cells are available for animals other than mouse and human. As a result, for these animals, it is currently practically impossible to create genetically modified animals having targeted mutations. The ES-cell like RPSCs can be manipulated to introduce desired targeted genetic modifications. The resulting engineered RPSCs can then be used to generate a cloned animal with the desired genetic modifications in its germ line, using methods described for ES cells in mouse. See Capecchi and Thomas, U.S. Pat. Nos. 5,487,992, 5,627,059, 5,631,153, and 6,204,061. Genetic engineering in animals has potentially great applications in a variety of animals, especially farm animals.

The somatic cell reprogramming methods of the present invention provides at least two methods for delivering optimized farm animals. In the first, somatic cell reprogramming can be used to capture the best available phenotype for a farm animal stock. The current technologies used to deliver optimized farm animals are based on selective breeding, and expansion from preferred breeding stocks. Animals that have been selected on the basis of superior characteristics, including, for example, meat content, egg production (in the case of poultry), feed conversion ratio, are used to breed large numbers of animals that are in turn used in the human food supply. This traditional process has profound inherent inefficiencies. The phenotype observed in an individual animal is often only partially transmitted in the progeny of that animal. Therefore, traditional breeding schemes are inefficient in capturing the very best phenotype in all of the progeny animals. In contrast, the reprogramming methods of the present invention provides a controlled and efficient way to achieve the same goal, by generating RPSCs from somatic cells of an animal with the desired characteristics. The RPSCs generated may be used immediately to generate cloned animals derived from the RPSCs. Known methods for generating mice from ES cells can be used for this procedure. Alternatively, the RPSCs generated may be cryopreserved and thawed in response to a grower's needs.

In the second method, somatic cells from an animal with the desired characteristics are reprogrammed to produce RPSCs. The RPSCs are further genetically engineered to introduce desired genetic modification(s), before being placed into a recipient embryo to produce desired progeny.

The reprogramming methods can also be used to rescue endangered species. Somatic cell reprogramming provides an efficient method to generate RPSCs from somatic cells of an endangered animal. The resulting RPSCs can be used immediately to expand the numbers of the endangered animal. Alternatively, the RPSCs can be cryopreserved to generate a RPSC stock for the endangered species, as a safeguard measure against extinction of the endangered species.

Methods for Gene Identification

The present invention provides methods for identifying a gene that activates the expression of an endogenous pluripotency gene in somatic cells. The methods comprise: transfecting the somatic cells of the present invention with a cDNA library prepared from ES cells or oocytes, selecting for cells that express the first selectable marker, and assessing the expression of the first endogenous pluripotency gene in the transfected cells that express the first selectable marker. The expression of the first endogenous pluripotency gene indicates that the cDNA encodes a gene that activates the expression of an endogenous pluripotency gene in somatic cells.

The methods are applicable for identifying a gene that activates the expression of at least two endogenous pluripotency genes in somatic cells. The somatic cells used in the methods further comprise a second endogenous pluripotency gene linked to a second selectable marker. The methods are modified to select for transfected cells that express both selectable markers, among which the expression of the first and the second endogenous pluripotency genes are assessed. The expression of both the first and the second endogenous pluripotency genes indicates that the cDNA encodes a gene that activates the expression of at least two pluripotency genes in somatic cells.

The methods are further applicable for identifying a gene that activates the expression of at least three endogenous pluripotency genes in somatic cells. The somatic cells used in the methods further comprise a third endogenous pluripotency gene linked to a third selectable marker. The methods are modified to select for transfected cells that express all three selectable markers, among which the expression of all three endogenous pluripotency genes are assessed. The expression of all three endogenous pluripotency genes indicates that the cDNA encodes a gene that activates the expression of at least three pluripotency genes in somatic cells.

The practice of the present invention will employ, unless otherwise indicated, conventional techniques of mouse genetics, developmental biology, cell biology, cell culture, molecular biology, transgenic biology, microbiology, recombinant DNA, and immunology, which are within the skill of the art. Such techniques are described in the literature. See, for example, Current Protocols in Cell Biology, ed. by Bonifacino, Dasso, Lippincott-Schwartz, Harford, and Yamada, John Wiley and Sons, Inc., New York, 1999; Manipulating the Mouse Embryos, A Laboratory Manual, $3^{rd}$ Ed., by Hogan et al., Cold Spring Harbor Laboratory Press, Cold Spring Harbor, N.Y., 2003; Gene Targeting: A Practical Approach, IRL Press at Oxford University Press, Oxford, 1993; and Gene Targeting Protocols, Human Press, Totowa, N.J., 2000. All patents, patent applications and references cited herein are incorporated in their entirety by reference.

EXEMPLIFICATION

The invention now being generally described, it will be more readily understood by reference to the following example, which are included merely for purposes of illustration of certain aspects and embodiments of the present invention, and are not intended to limit the invention.

Example. Oct4-Induced Fibroblasts are More Susceptible to Reprogramming than Unduced Fibroblasts as Demonstrated by Nuclear Transfer Experiment A. Generation of Transgenic Mouse Carrying an Inducible Oct4 Transgene An inducible Oct4 allele is constructed as the following: first, two integration vectors are constructed. The first integration vector, inducible Oct4 integration vector, contains an Oct4 gene driven by a tetracycline-inducible promoter (Tet-Op). The Tet-Op-Oct4 cassette is flanked by a splice-acceptor double poly-A signal (SA-dpA) at its 5' end and a SV40 polyA tail (SV40-pA) at its 3' end. The second integration vector, tetracycline activator integration vector, contains a mutant form of tetracycline activator, M2-rtTA, which is more responsive to doxycycline (Dox) induction than the wild type activator. (Urlinger S. et al., 2000)

The two integration vectors are introduced into V6.5 ES cells: the inducible Oct4 integration vector and the tetracycline activator integration vector are introduced into the Collagen locus and the Rosa26 locus respectively via site-specific integration, as shown in FIG. 1. The resulting ES cells are used to make Oct4-inducible mice by tetraploid complementation.

B. Expression of the Inducible Oct4 Transgene

Fibroblasts derived from tail biopsies of the Oct4-inducible mice were cultured. A fraction of the cultured fibroblasts were induced with doxycycline for 3 days (at 2 microgram/ml), and Oct4 expression was detected by Northern blot and Western blot analysis. As shown in FIG. 2, the Oct4 expression level in fibroblasts treated with doxycycline is comparable to the Oct4 expression level in ES cells, and undetectable in fibroblasts not treated with doxycycline. The expression results demonstrate that the inducible Oct4 transgene is expressed as planned.

C. Nuclear Transfer Experiment

Nuclear transfer was performed on fibroblasts derived from tail biopsies of mice that carry the inducible Oct4 transgene. Dox induction was for 24 hours prior to nuclear transfer. Cloned embryos were then activated and cultured to the blastocyst stage to derive ES cells as described previously (Hochedlinger and Jaenisch, 2002). As shown in Table 1, on average, blastocyst formation and ES cell derivation (as measured as a fraction of eggs with pronucleus formation) is more efficient from Oct4 induced fibroblast than from uninduced fibroblasts. This result demonstrated that induced Oct4 expression in somatic cells such as fibroblasts make these cells more susceptible to reprogramming.

One skilled in the art readily appreciates that the present invention is well adapted to carry out the objects and obtain the ends and advantages mentioned, as well as those inherent therein. The methods, systems and kits are representative of preferred embodiments, are exemplary, and are not intended as limitations on the scope of the invention. Modifications therein and other uses will occur to those skilled in the art. These modifications are encompassed within the spirit of the invention and are defined by the scope of the claims. It will be readily apparent to a person skilled in the art that varying substitutions and modifications may be made to the invention disclosed herein without departing from the scope and spirit of the invention.

TABLE 1

In vitro development of clones derived from Oct4-induced fibroblasts

| Expt. | Oct4 | eggs w/PN | Blastocysts (% PN) | | ES lines (% PN) | |
|---|---|---|---|---|---|---|
| #1 | − | 22 | 5 (23%) | 19% | 0 (0%) | 3% |
| #2 | − | 35 | 5 (14%) | | 2 (6%) | |
| #3 | + | 37 | 10 (27%) | 24% | 2 (5%) | 7% |
| #4 | + | 47 | 10 (21%) | | 4 (9%) | |

PN . . . ProNucleus formation
Nuclear transfer was performed on fibroblasts derived from tail biopsies of mice that carry the inducible Oct4 transgene. Dox induction was for 24 hours prior to nuclear transfer. Cloned embryos were then activated and cultured to the blastocyst stage to derive ES cells as described previously (Hochedlinger and Jaenisch, Nature, 2002). These preliminary results show that on average blastocyst formation and ES cell derivation is more efficient from Oct4 induced than from uninduced fibroblasts.

REFERENCES

Avilion, J., et al., Nat. Biotechnol. 20: 1240-45 (2003)
Gossen M. et al., Transcriptional activation by tetracyclines in mammalian cells,
Science 268: 1766-1769 (1995).
Hanna, L. A., et al., Genes Dev. 16: 2650-61 (2002).
Hochedlinger and Jaenisch, Nature 415: 1035-1038 (2002).
Hogan et al., Cold Spring Harbor Laboratory Press, Cold Spring Harbor, N.Y., 2003
Ihle, J. H., Cell 84: 331-334 (1996)
Munsie M. J., et al., Curr. Biol. 10: 989 (2000).
Shmblott, M. J., et al., Derivation of pluripotent stem cells from cultured human primordial germ cells. Proc. Natl. Acad. Sci. USA 95: 13726-13731 (1998)
Smith A. G., et al. Nature 336: 688-690 (1988)
Tan, D. S., Foley, M. A., Shair, M. D. & Schreiber, S. L. J. Am. Chem. Soc. 120, 8565-8566 (1998).
Thomson, J. A., et al., Embryonic stem cell lines derived from human blastocysts. Science, 282: 1145-1147 (1998).
Urlinger S, Baron U, Thellmann M, Hasan M T, Bujard H, Hillen W. Proc. Natl. Acad. Sci. USA. 97(14):7963-8 (2000). Exploring the sequence space for tetracycline-dependent transcriptional activators: novel mutations yield expanded range and sensitivity.

William R. L., et al., Nature 336: 684-687 (1988)

Yamada, Y., Miyashita, T., Savagner, P., Horton, W., Brown, K. S., Abramczuk, J., Xie, H. X., Kohno, K., Bolander, M. and Bruggeman, L. (1990). Regulation of the collagen II gene in vitro and in transgenic mice. *Ann. New York Acad. Sci.* 580, 81-87

Zambrowicz B. P. et al., Disruption of overlapping transcripts in the ROSA bgeo 26 gene trap strain leads to widespread expression of b-galatosidase in mouse embryos and hematopoietic cells. Proc. Natl. Acad. Sci. USA 94: 3789-3794 (1997).

What is claimed is:

1. A method of making a somatic cell more susceptible to reprogramming to a cell having a less differentiated state, comprising:

obtaining a somatic cell that comprises an exogenously introduced polynucleic acid encoding Oct4 protein, and an exogenously introduced polynucleic acid encoding Sox2 or Nanog protein;

wherein the exogenously introduced polynucleic acids result in making the somatic cell more susceptible to reprogramming to a less differentiated state.

2. The method of claim 1, the step of obtaining further comprises:

introducing an exogenous polynucleic acid encoding Oct4 protein, and an exogenously introduced polynucleic acid encoding Sox2 or Nanog protein into the somatic cell; wherein one or both of the polynucleic acids is operatively linked to at least one heterologous regulatory sequence.

3. The method of claim 1 or 2, further comprising:

contacting the somatic cell with a candidate agent of interest with respect to its potential to reprogram a somatic cell.

4. The method of claim 3, wherein the candidate agent of interest is a DNA methylation inhibitor, a histone deacetylase inhibitor or PD098059.

5. The method of claim 1, wherein the exogenous polynucleic acids increase Oct4 expression in the somatic cell.

6. The method of claim 1, wherein the somatic cell is a mammalian cell.

7. The method of claim 1, wherein the somatic cell is a human cell or a mouse cell.

8. The method of claim 1, wherein the somatic cell is an adult stem cell.

9. The method of claim 8, wherein the adult stem cell is selected from the group consisting of: a hematopoietic stem cell, a neural stem cell, and a mesenchymal stem cell.

* * * * *

UNITED STATES PATENT AND TRADEMARK OFFICE
CERTIFICATE OF CORRECTION

PATENT NO. : 10,017,744 B2
APPLICATION NO. : 15/588062
DATED : July 10, 2018
INVENTOR(S) : Rudolf Jaenisch et al.

It is certified that error appears in the above-identified patent and that said Letters Patent is hereby corrected as shown below:

In the Specification

At Column 1, Line 19 through Line 23, delete:
"GOVERNMENTAL FUNDING
This invention was made with government support under R37 CA84198 awarded by the National Institutes of Health. The government has certain rights in the invention."

Signed and Sealed this
Third Day of January, 2023

Katherine Kelly Vidal
*Director of the United States Patent and Trademark Office*